(12) United States Patent
Igarashi et al.

(10) Patent No.: US 8,987,253 B2
(45) Date of Patent: *Mar. 24, 2015

(54) COMPOUND HAVING ACTIVITY OF BLOCKING NMDA RECEPTOR CHANNEL, AND PHARMACEUTICAL AGENT USING THE SAME

(71) Applicant: National University Corporation Chiba University, Chiba (JP)

(72) Inventors: Kazuei Igarashi, Chiba (JP); Hiromitsu Takayama, Chiba (JP)

(73) Assignee: National University Corporation Chiba University, Chiba (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/906,424

(22) Filed: May 31, 2013

(65) Prior Publication Data

US 2013/0274248 A1    Oct. 17, 2013

Related U.S. Application Data

(63) Continuation of application No. 12/298,564, filed as application No. PCT/JP2007/059108 on Apr. 26, 2007, now Pat. No. 8,476,258.

(30) Foreign Application Priority Data

Apr. 28, 2006  (JP) ................................ 2006-124858

(51) Int. Cl.
| | |
|---|---|
| *C07D 223/18* | (2006.01) |
| *A61K 31/55* | (2006.01) |
| *C07D 223/26* | (2006.01) |
| *A61K 31/166* | (2006.01) |
| *A61K 31/403* | (2006.01) |
| *C07C 235/84* | (2006.01) |
| *C07D 209/86* | (2006.01) |
| *C07D 223/28* | (2006.01) |

(52) U.S. Cl.
CPC ............ *C07D 223/26* (2013.01); *A61K 31/166* (2013.01); *A61K 31/403* (2013.01); *A61K 31/55* (2013.01); *C07C 235/84* (2013.01); *C07D 209/86* (2013.01); *C07D 223/28* (2013.01)
USPC .......................................... 514/217; 540/589

(58) Field of Classification Search
CPC ................................................... C07D 223/18
USPC ........................................................ 540/589
See application file for complete search history.

(56) References Cited

U.S. PATENT DOCUMENTS

| | | |
|---|---|---|
| 2004/0063147 A1 | 4/2004 | Natrajan et al. |
| 2009/0105223 A1 | 4/2009 | Igarashi et al. |

FOREIGN PATENT DOCUMENTS

| | | |
|---|---|---|
| EP | 1 085 011 A1 | 3/2001 |
| WO | WO 2007/105786 A1 | 9/2007 |

OTHER PUBLICATIONS

Nakanishi et al. Structure-Binding Relation of Philanthotoxins from Nicotinic Acetylcholine Receptor Binding Assay. 1997, Bioorganic and Medicinal Chemistry, 5, 1969-1988.*
Supplementary European Search Report issued in corresponding European Patent Application No. EP 07742543.7 dated Jul. 15, 2009 (4 pages).
Takayama et al., "Design, synthesis, and biological evaluation of tricyclic heterocycle-tetraamine conjugates as potent NMDA channel blockers," Bioorganic & Medicinal Chemistry Letters, vol. 17, No. 17, Aug. 4, 2007, pp. 4729-4732 (4 pages).
Jin et al., "Comparative Studies of Anthraquinone- and Anthracene-Tetraamines as Blockers of $N$-Methyl-$_D$-aspartate Receptors," The Journal of Pharmacology and Experimental Therapeutics, vol. 320, No. 1, Jan. 2007, pp. 47-55 (9 pages).
Nakanishi et al., "Structure-Binding Relation of Philanthotoxins from Nicotinic Acetylcholine Receptor Binding Assay," Bioorganic and Medicinal Chemistry, vol. 5, 1997, pp. 1969-1988 (20 pages).
West, Anthony R., "Solid State Chemistry and its Applications," Wiley, New York, 1988, pp. 358 and 365 (3 pages).
Morissette et al., "High-throughput crystallization: polymorphs, salst, co-crystals and solvates of pharmaceutical solids," Advanced Drug Delivery Reviews, 2004, vol. 56, pp. 275-300 (26 pages).
Notification of Transmittal of Translation of the International Preliminary Report on Patentability (Chapter I or Chapter II of the Patent Cooperation Treaty), International Preliminary Report on Patentability, and Translation of the Written Opinion of the International Searching Authority for corresponding International Patent Application No. PCT/JP2007/059108 dated Nov. 27, 2008 (9 pages).
Carrington et al., "Inhibition of Growth of B16 Murine Melanoma Cells by Novel Spermine Analogues," Pharmaceutical Sciences, vol. 2, No. 1, 1996, pp. 25-27 (3 pages).
Kashiwagi et al., "Anthraquinone Polyamines: Novel Channel Blockers to Study $N$-Methyl-D-Aspartate Receptors," The Journal of Pharmacology and Experimental Therapeutics, vol. 309, No. 3, 2004, pp. 884-893 (10 pages).
Igarashi et al., "Benzyl-polyamines: Novel, Potent $N$-Methyl-D-aspartate Receptor Antagonists,"The Journal of Pharmacology and Experimental Therapeutics, vol. 283, No. 2, 1997, pp. 533-540 (8 pages).

\* cited by examiner

*Primary Examiner* — Brian McDowell
(74) *Attorney, Agent, or Firm* — Kilyk & Bowersox, P.L.L.C.

(57) ABSTRACT

[PROBLEMS] To provide a novel compound having NMDA receptor channel blocking activity, and also a pharmaceutical agent comprising the compound.
[MEANS FOR SOLVING PROBLEMS] A pharmaceutical agent for the treatment or prevention of a disease caused by overexcitation of an NMDA receptor, which comprises a compound having NMDA receptor channel blocking activity and represented by the formula (1), a salt thereof, or a hydrate of the compound or the salt.

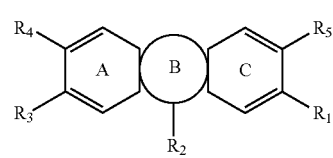

(1)

7 Claims, 4 Drawing Sheets

COMPOUND HAVING ACTIVITY OF BLOCKING NMDA RECEPTOR CHANNEL, AND PHARMACEUTICAL AGENT USING THE SAME

This application is a continuation of U.S. patent application Ser. No. 12/298,564, filed Oct. 27, 2008, which in turn is a National Stage Application of PCT/JP2007/059108, filed Apr. 26, 2007, which claims priority to JP 2006-124858 filed Apr. 28, 2006.

TECHNICAL FIELD

The present invention relates to compounds having activity of blocking an NMDA receptor channel, and pharmaceutical agents using the same.

BACKGROUND ART

Cerebrovascular disorders such as cerebral infarction and cerebral hemorrhage, and diseases that strongly affect higher brain functions such as Alzheimer's disease exhibit poor prognosis, and bring decreased QOL (Quality of Life) on elderly people and further psychological stress on caretakers. Several pharmaceutical agents for improving brain functions have been developed and marketed to date. However, a sufficient therapeutic effect has not yet been obtained by using any of them. Thus, new and more effective agents for improving brain functions and agents for preserving brain functions are expected to be developed rapidly.

Meanwhile, N-methyl-D-aspartic acid (hereafter referred to as "NMDA") receptor, which is one kind of receptor for glutamic acid that is an excitatory neurotransmitter, is known to transport $Ca^{2+}$ to neuron and thereby strongly participate in memory formation and in development of symptoms in cerebral ischemia.

The present inventors already reported in the Non-Patent Document 1 shown below that NMDA receptors expressed on *Xenopus oocytes* followed by contacting with a plurality of polyamine derivatives and measuring a change in electric potential resulted in a finding that a polyamine derivative having an anthraquinone skeleton showed a significant channel blocking activity (see Non-Patent Document 1 shown below).

Non-Patent Document 1: J. Pharm. Exp. Ther., 309:884-893

DISCLOSURE OF THE INVENTION

Problem to be Solved by the Invention

However, even in the technology described in the above-mentioned Non-Patent Document 1, intensity of channel blocking activity remains to be improved.

Thus, an object of the present invention is to provide a novel compound which has NMDA receptor channel blocking activity, and a pharmaceutical agent comprising the compound.

Means for Solving the Object

Thus, a means of the present invention relate to, as one means, a pharmaceutical agent for use in medical treatment or prevention of diseases caused by overexcitation of NMDA receptors, which comprises a compound having NMDA receptor channel blocking activity and represented by the following formula (1), a salt thereof, or a hydrate of the compound or the salt.

(1)

(where, B-ring condensed to A-ring and C-ring is quinone, benzene, pyrrole, pyridine, 1,4-dihydropyridine, azepine, 4,5-dihydroazepine or 1,4-thiazine. $R_1$-$R_5$ are each independently formyl, acyl, hydrogen, alkyl, alkoxy, halogen, hydroxy, amino, aryl or carboxamido, and at least either of $R_1$ or $R_2$ is a carboxamide group having a polyamine structure containing three or more amino groups except an amino group of the carboxamido group. $R_1$-$R_5$ may be identical or different).

Further, in that means, the pharmaceutical agent preferably comprises a compound having NMDA receptor channel blocking activity and represented by the following formula (2), a salt thereof, or a hydrate of the compound or the salt, but not limited thereto.

[chemical formula 2]

(2)

Further, in that means, the pharmaceutical agent preferably comprises a compound having NMDA receptor channel blocking activity and represented by the following formula (3), a salt thereof, or a hydrate of the compound or the salt, but not limited thereto.

[chemical formula 3]

(3)

Further, in that means, the pharmaceutical agent preferably comprises a compound having NMDA receptor channel blocking activity and represented by the following formula (4), a salt thereof, or a hydrate of the compound or the salt, but not limited thereto.

[chemical formula 4]

(4)

Further, in that means, the pharmaceutical agent preferably comprises a compound having NMDA receptor channel blocking activity and represented by the following formula (5), a salt thereof, or a hydrate of the compound or the salt, but not limited thereto.

[chemical formula 5]

(5)

Disorders caused by overexcitation of NMDA receptors are preferably cerebrovascular disorder, cerebral infarction, cerebral hemorrhage, Alzheimer's disease, central neurodegeneration, traumatic brain damage, traumatic spinal cord injury or demyelinating disease, or sequelae of these diseases, but not limited thereto Further, an another means of the present invention relates to a compound represented by the following formula (1):

[chemical formula 6]

(1)

(where, B-ring condensed to A-ring and C-ring is quinone, benzene, pyrrole, pyridine, 1,4-dihydropyridine, azepine, 4,5-dihydroazepine or 1,4-thiazine. $R_1$-$R_5$ are each independently formyl, acyl, hydrogen, alkyl, alkoxy, halogen, hydroxy, amino, aryl or carboxamido, and at least either of $R_1$ or $R_2$ is a carboxamide group having a polyamine structure containing three or more amino groups except an amino group of the carboxamido group. $R_1$-$R_5$ may be identical or different).

Further, in that means, the compound is preferably represented by the following formula (2), but not limited thereto.

[chemical formula 7]

(2)

Further, in that means, the compound is preferably represented by the following formula (3), but not limited thereto.

[chemical formula 8]

(3)

Further, in that means, the compound is preferably represented by the following formula (4), but not limited thereto.

[chemical formula 9]

(4)

Further, in that means, the compound is preferably represented by the following formula (5), but not limited thereto.

[chemical formula 10]

(5)

Advantage of the Invention

As mentioned above, the present invention can provide novel compounds having NMDA receptor channel blocking activity, pharmaceutical agents comprising the compounds, and screening methods using the compounds.

DETAILED DESCRIPTION OF THE INVENTION

Embodiments

One embodiment of the present invention is a compound having NMDA receptor channel blocking activity and represented by the following formula (1):

[chemical formula 11]

(1)

In the aforementioned formula (1), B-ring condensed to A-ring and C-ring is quinone, benzene, pyrrole, pyridine, 1,4-dihydropyridine, azepine, 4,5-dihydroazepine or 1,4-thiazine. $R_1$-$R_5$ are each independently formyl, acyl, hydrogen, alkyl, alkoxy, halogen, hydroxy, amino, aryl or carboxamido, and at least either of $R_1$ or $R_2$ is a carboxamide group having a polyamine structure containing three or more amino groups except an amino group of the carboxamido group. $R_1$-$R_5$ may be identical or different.

The present inventors made intensive studies for novel compounds that show NMDA receptor channel blocking activity, and found out that a polyamine inhibited NMDA receptor activity and suppressed intracellular calcium influx.

The present inventors made a further detailed investigation, and reached a compound represented by the above-mentioned formula (1). The term "polyamine" described herein denotes a compound having two or more amino groups in a molecule. Further, the phrase "polyamine structure" denotes a structure having two or more amino groups, and includes, but not limited to, putrescine, cadaverine, spermidine, 1,3-diaminopropane, caldine, homospermidine, 3-aminopropyl-cadaverine, norspermine, homospermine, thermospermine, caldopentamine. The more preferable polyamine structure is homospermine. "The polyamine structure containing three or more amino groups except an amino group of the carboxamido group" is required for NMDA receptor channel blocking activity. Homospermine is preferable for such a polyamine structure, but not limited thereto.

The compound represented by the aforementioned formula (1) can be synthesized by a conventional method, as clearly shown in examples described later, but it is not limited to the synthesized one as far as it is available.

Another embodiment of the present invention is a pharmaceutical agent comprising as an active ingredient a compound having NMDA receptor channel blocking activity and represented by the aforementioned formula (1), a salt thereof, or a hydrate of the compound or the salt.

The aforementioned pharmaceutical agent can be supplied, in addition to the aforementioned compound having NMDA receptor channel blocking activity, with various pharmaceutically acceptable formulation components such as carriers, binders, stabilizers, excipients, diluents, pH buffers, disintegrators, solubilizers, dissolution auxiliaries, and isotonizers. The compound having NMDA receptor channel blocking activity can be administrated orally or parenterally at an appropriate dosage depending on gender, body weight and symptoms of a patient for prevention or treatment. That is to say, it can be administrated in a conventional administration form. For example, it can be orally administrated in a dosage form such as powders, granules, capsules, syrups and suspensions. Alternatively, it can be parenterally administrated in a dosage form for injection such as solutions, emulsions and suspensions, or intranasally administrated in a spray form.

Consequently, the novel compound having NMDA receptor channel blocking activity and the pharmaceutical agent comprising the compound can be provided.

EXAMPLE

The present invention may be explained more particularly with examples showing activity of compounds of the aforementioned embodiment; however, the present invention is not limited to these examples.

Production Example 1

Synthesis of Anthraquinone Homospermine (AQ444)

Anhydrous triethylamine (0.46 mL) and para-nitrophenol (238 mg) were added to an anhydrous methylene chloride solution (10 mL) of anthraquinone 2-carbonyl chloride (300 mg), and stirred for 3 hours under an argon stream at room temperature. The reaction solution was poured into an aqueous 1N sodium hydroxide solution and extracted with chloroform, 5% methanol/chloroform mixed solution. An organic layer thus obtained was washed with a saturated saline, dried on magnesium sulfate, followed by concentration under a reduced pressure to form solid precipitate, which was then filtered by suction to yield a yellowish-white solid of anthraquinone 2-nitrophenyl ester (270 mg, 65% yield). $^1$H-MNR and $^{13}$C-NMR spectral data and EI-MS data of the yellowish-white solid are shown below.

$^1$H-NMR (500 MHz, CDCl$_3$)

δ 9.13 (1H, d, J=1.5 Hz), 8.59 (1H, dd, J=7.9, 1.5 Hz), 8.50 (1H, d, J=7.9 Hz), 8.40-8.36 (4H, overlapped), 7.88 (2H, m), 7.50 (2H, m).

$^{13}$C-NMR (125 MHz, CDCl$_3$)

δ 182.3, 182.1, 162.8, 155.2, 145.7, 136.9, 135.1, 134.72, 134.66, 133.8, 133.5, 133.3, 129.3, 128.0, 127.60, 127.56, 125.4, 122.5.

EI-MS m/z (%) 373 (M$^+$, 1), 235 (100).

Next, an anhydrous chloroform solution (2.5 mL) of anthraquinone 2-paranitrophenyl ester (11 mg) was added to an anhydrous chloroform solution (2.5 mL) of 5,10-bis(2-nitrobenzene sulfonyl)-5,10-diaza-1,14-tetradecanediamine (36 mg), and stirred for 4 hours under an argon stream at room temperature, and then for 1 hour at 50° C. The reaction solution was directly applied to an amino silica gel column (methanol/chloroform mixed solution) for purification to get a 2% methanol/chloroform eluate, which was then concentrated under a reduced pressure to yield an AQ444 derivative (15 mg, 60% yield). The tetraamine derivative used in large excess as a raw material was recovered. $^1$H-MNR spectral data, $^{13}$C-NMR spectral data, and FAB-MS data of the AQ444 derivative are shown below.

$^1$H-NMR (400 MHz, CDCl$_3$)

δ 8.59 (1H, d, J=1.7 Hz), 8.33 (1H, d, J=8.1 Hz), 8.31 (2H, m), 8.25 (1H, d, J=8.1, 1.7 Hz), 7.99 (2H, m), 7.83 (2H, m), 7.72-7.60 (6H, overlapped), 3.51 (2H, m), 3.33-3.22 (8H, overlapped), 2.64 (2H, dd, J=7.0, 7.0 Hz), 1.72-1.44 (10H, overlapped), 1.35 (2H, m).

$^{13}$C-NMR (150 MHz, CDCl$_3$)

δ 182.6, 182.0, 165.9, 148.0, 139.8, 135.1, 134.5, 134.4, 133.62, 133.56, 133.5, 133.4, 133.3, 133.1, 131.8, 131.7, 130.72, 130.68, 127.9, 127.5, 125.3, 124.2, 47.6, 47.5, 47.4, 46.9, 45.4, 41.7, 39.7, 30.6, 26.6, 26.0, 25.6, 25.4, 25.1.

FAB-MS (NBA)

m/z 835 (MH$^+$).

Then, calcium carbonate (24 mg) and thiophenol (74) were added to an anhydrous DMF solution (1.0 mL) of the AQ444 derivative (48 mg) obtained as mentioned above, and stirred for 13 hours under an argon stream at room temperature. The reaction solution was directly applied to an amino silica gel column (methanol/chloroform mixed solution) for purification to get 5%, 10% and 20% methanol/chloroform eluates, which were then concentrated under a reduced pressure to yield AQ444 (19 mg, 70% yield). The Structural formula (2) of AQ444 thus obtained is shown below as well as UV spectrum, $^1$H-NMR spectral data, $^{13}$C-NMR spectral data, and FAB-MS data.

UV (MeOH)

λ$_{max}$ 326.0, 256.5, 210.0 nm.

$^1$H-NMR (500 MHz, CDCl$_3$)

δ 8.60 (1H, br-d, J=1.5 Hz), 8.38 (1H, d, J=8.1 Hz), 8.37-8.30 (4H, overlapped), 7.83 (2H, m), 3.52 (1H, br-ddd, J=5.9, 5.9, 5.9 Hz), 2.72 (2H, dd, J=6.5, 6.5 Hz), 2.67 (1H, dd, J=6.6, 6.6 Hz), 2.65-2.60 (3H, overlapped), 2.56-2.50 (4H, overlapped), 1.78 (2H, br-quin, J=6.3 Hz), 1.67 (2H, br-quin, J=6.3 Hz), 1.64-1.40 (8H, overlapped).

$^{13}$C-NMR (125 MHz, CDCl$_3$)

δ 182.6, 182.5, 165.7, 140.2, 134.9, 134.42, 134.35, 133.4133.3, 127.8, 127.4, 127.3, 125.1, 51.9, 49.8, 49.7, 49.6, 49.1, 42.1, 40.3, 36.3, 31.5, 27.9, 27.8, 27.7, 27.4.

FAB-MS (NBA+NaCl)

m/z 465 (MH$^+$).

Production Example 2

Synthesis of Carbazole Spermine

Anhydrous triethylamine (546 μL) and para-nitrophenol (272 mg) were added to an anhydrous methylene chloride solution (10 mL) of carbazole N-carbonyl chloride (300 mg), and stirred for 3.5 hours under an argon stream at room temperature. The reaction solution was poured into an aqueous 1N sodium hydroxide solution and extracted with chloroform, 5% methanol/chloroform mixed solution. An organic layer thus obtained was washed with a saturated saline, dried on magnesium sulfate, and then concentrated under a reduced pressure to a yield yellowish-white solid of carbazole N-paranitrophenyl ester (401 mg, 92% yield). $^1$H-MNR spectral data of the yellowish-white solid thus obtained is shown below.

$^1$H-NMR (400 MHz, CDCl$_3$)

δ 8.39 (2H, d-like, J=10.1 Hz), 8.32 (2H, d-like, J=7.5 Hz), 8.03 (2H, br-d, J=7.5 Hz), 7.52 (2H, d-like, J=10.1 Hz), 7.57 (2H, ddd, J=7.5, 7.5, 1.2 Hz), 7.45 (2H, ddd, J=7.5, 7.5, 1.2 Hz).

Next, an anhydrous chloroform solution (6.5 mL) of carbazole N-paranitrophenyl ester (30 mg) was added to an anhydrous chloroform solution (6.5 mL) of spermine (40 mg), and stirred for 3.5 hours under an argon stream at room temperature. The reaction solution was directly applied to an amino silica gel column (methanol/chloroform mixed solution) for purification to get a 5% methanol/chloroform eluate, which was then concentrated under a reduced pressure to yield carbazole spermine (25 mg, 70% yield). The structural formula (3) of carbazole spermine thus obtained is shown below, as well as $^1$H-NMR spectral data, $^{13}$C-NMR spectral data, and FAB-MS data.

[chemical formula 12]

(2)

[chemical formula 13]

(3)

¹H-NMR (500 MHz, CDCl₃)

δ 8.08 (2H, d, J=7.8 Hz), 8.02 (2H, d, J=7.8 Hz), 7.45 (2H, ddd, J=7.8, 7.8, 0.9 Hz), 7.31 (2H, ddd, J=7.8, 7.8, 0.9 Hz), 3.69 (2H, br-dd, J=10.4, 5.8 Hz), 2.83 (2H, br-dd, J=5.6, 5.6 Hz), 2.69 (2H, dd, J=6.9, 6.9 Hz), 2.52 (4H, overlapped), 2.35 (2H, br-dd, J=6.7, 6.7 Hz), 1.84 (2H, br-quin, J=6.0 Hz), 1.54 (2H, quin, J=6.7 Hz), 1.28-1.19 (4H, m).

¹³C-NMR (125 MHz, CDCl₃)

δ 152.8, 138.3, 126.6, 124.8, 121.8, 119.9, 113.8, 49.8, 49.7, 49.3, 47.7, 41.6, 40.5, 33.6, 28.1, 27.6, 27.5.

FAB-MS (NBA)

m/z 396 (MH⁺).

Production Example 3

Synthesis of Dibenzoazepine Homospermine (DBA444)

An anhydrous methylene chloride solution (1.5 mL) of commercially available 5H-dibenzo[b,f]azepine-5-carbonyl chloride (24.5 mg) was added to an anhydrous methylene chloride solution (6.5 mL) of 5,10-bis(2-nitrobenzene sulfonyl)-5,10-diaza-1,14-tetradecane diamine (115 mg), and stirred for 2 hours under an argon stream at room temperature. The reaction solution was directly applied to amino silica gel column (methanol/chloroform mixed solution) for purification to get an 1% methanol/chloroform eluate, which was then concentrated under a reduced pressure to yield a DBA444 derivative (60.1 mg, 76% yield). Further, the tetraamine derivative used in large excess as a raw material was recovered. ¹H-NMR spectral data, ¹³C-NMR spectral data, and FAB-MS data of the DBA444 derivative are shown below.

¹H-NMR (400 MHz, CDCl₃)

δ 7.98-7.94 (2H, m), 7.70-7.63 (4H, overlapped), 7.61-7.57 (2H, m), 7.45-7.40 (4H, overlapped), 7.40-7.30 (4H, overlapped), 6.92 (2H, s), 4.35 (1H, br-dd, J=5.8, 5.8 Hz), 3.26-3.22 (6H, overlapped), 3.19 (2H, dd, J=7.6, 7.6 Hz), 3.09 (2H, br-ddd, J=6.5, 6.5, 6.5 Hz), 2.65 (2H, dd, J=7.0, 7.0 Hz), 1.58-1.31 (12H, overlapped).

¹³C-NMR (100 MHz, CDCl₃)

δ 156.3, 147.96, 147.94, 140.0, 135.2, 133.4, 133.3, 131.70, 131.65, 130.60, 130.55, 130.4, 129.6, 129.4, 129.1, 127.6, 124.1, 124.0, 47.3, 47.0, 46.8, 46.7, 41.6, 39.7, 30.5, 27.3, 25.6, 25.3, 25.0.

FAB-MS (NBA)

m/z 820 (MH⁺).

Then, calcium carbonate (92.9 mg) and thiophenol (55.2 μL) were added to an anhydrous DMF solution (4.5 mL) of the DBA444 derivative (183.5 mg) obtained as mentioned above, and stirred for 2.5 hours under an argon stream at room temperature. The reaction solution was directly applied to amino silica gel column (methanol/chloroform mixed solution) for purification to get a 5% methanol/chloroform eluate, which was then concentrated under a reduced pressure to yield DBA444 (62.4 mg, 62% yield). The structural formula (4) of DBA444 thus obtained is shown below as well as data of UV spectrum, ¹H-NMR spectral data, ¹³C-NMR spectral data, and FAB-MS data.

[chemical formula 14]

(4)

UV (MeOH)

λ_max 285.5, 247.5 (sh), 213.5 nm.

¹H-NMR (400 MHz, CDCl₃)

δ 7.46-7.40 (4H, overlapped), 7.38-7.30 (4H, overlapped), 6.91 (2H, s), 4.46 (1H, br-dd, J=5.7, 5.7 Hz), 3.13 (2H, br-ddd, J=6.3, 6.3, 6.3 Hz), 2.70 (2H, dd, J=6.7, 6.7 Hz), 2.63-2.59 (2H, overlapped), 2.57-2.53 (2H, overlapped), 1.56-1.46 (8H, overlapped), 1.43-1.37 (4H, overlapped).

¹³C-NMR (100 MHz, CDCl₃)

δ 156.3, 140.1, 135.3, 130.4, 129.6, 129.3, 129.2, 127.5, 49.74, 49.72, 49.6, 49.3, 42.0, 40.4, 31.5, 27.94, 27.85, 27.84, 27.4, 27.1.

FAB-MS (NBA)

m/z 450 (MH⁺).

Production Example 4

Synthesis of Dihydrodibenzoazepine Homospermine (DDBA444)

An anhydrous methylene chloride solution (8.0 mL) of commercially available 10,11-dihydro-dibenzo[b,f]azepine-5-carbonyl chloride (84.9 mg) was added to an anhydrous methylene chloride solution (22.0 mL) of 5,10-bis(2-nitrobenzene sulfonyl)-5,10-diaza-1,14-tetradecanediamine (396.0 mg), and stirred for 19 hours under an argon stream at room temperature. The reaction solution was directly applied to an amino silica gel column (methanol/chloroform mixed solution) for purification to get a 1% methanol/chloroform eluate, which was then concentrated under a reduced pressure to yield a DDBA444 derivative (257.5 mg, 95% yield). Further, the tetraamine derivative used in large excess as a raw material was recovered. ¹H-NMR spectral data, ¹³C-NMR spectral data, and FAB-MS data of the DDBA444 derivative are shown below.

¹H-NMR (400 MHz, CDCl₃)

δ 7.98-7.95 (2H, m), 7.70-7.64 (4H, overlapped), 7.61-7.56 (2H, m), 7.36-7.33 (2H, m), 7.22-7.20 (6H, overlapped), 4.60 (1H, br-dd, J=6.0, 6.0 Hz), 3.26-3.15 (10H, overlapped), 2.65 (2H, dd, J=6.8, 6.8 Hz), 1.58-1.33 (16H, overlapped).

¹³C-NMR (100 MHz, CDCl₃)

δ 156.4, 147.9, 140.5, 137.2, 133.4, 133.3, 131.69, 131.64, 130.6, 130.5, 130.3, 128.9, 127.8, 127.0, 124.1, 124.0, 47.3, 47.0, 46.8, 46.7, 41.5, 39.9, 30.7, 30.5, 27.4, 25.5, 25.4, 25.0.

FAB-MS (NBA)

m/z 822 (MH⁺).

Then, cesium carbonate (237.8 mg) and thiophenol (59.9 μL) were added to an anhydrous DMF solution (4.5 mL) of the DDBA444 derivative (200.0 mg) obtained as mentioned above, and stirred for 3 hours under an argon stream at room temperature. The reaction solution was directly applied to an amino silica gel column (methanol/chloroform mixed solution) for purification to get a 5% methanol/chloroform eluate, which was then concentrated under a reduced pressure. The residues thus obtained were applied to an alumina column (ethanol/chloroform/concentrated ammonia water [=5/95/1] mixed solution) for purification to get an eluate, which was then concentrated under a reduced pressure to yield DDBA444 (68.8 mg, 63% yield). The structural formula (5) of DDBA444 thus obtained is shown below as well as UV spectrum, $^{1}$H-NMR spectral data, $^{13}$C-NMR spectral data, and FAB-MS data.

[chemical formula 15]

(5)

UV (MeOH)
$\lambda_{max}$ 239.5 (sh), 203.0 nm.
$^{1}$H-NMR (400 MHz, CDCl$_3$)
δ 7.38-7.36 (2H, m), 7.23-7.20 (6H, overlapped), 4.69 (1H, br-dd, J=5.4, 5.4 Hz), 3.22 (2H, br-ddd, J=6.3, 6.3, 6.3 Hz), 2.70 (2H, dd, J=6.5, 6.5 Hz), 2.63-2.54 (8H, overlapped), 1.63-1.56 (4H, overlapped), 1.53-1.43 (12H, overlapped).
$^{13}$C-NMR (150 MHz, CDCl$_3$)
δ 156.5, 140.7, 137.3, 130.4, 129.1, 127.8, 127.1, 49.90, 49.87, 42.2, 40.7, 31.6, 30.9, 28.2, 28.0, 27.5, 27.3.
FAB-MS (NBA)
m/z 452 (MH$^+$).

Example 1

Figure 1:
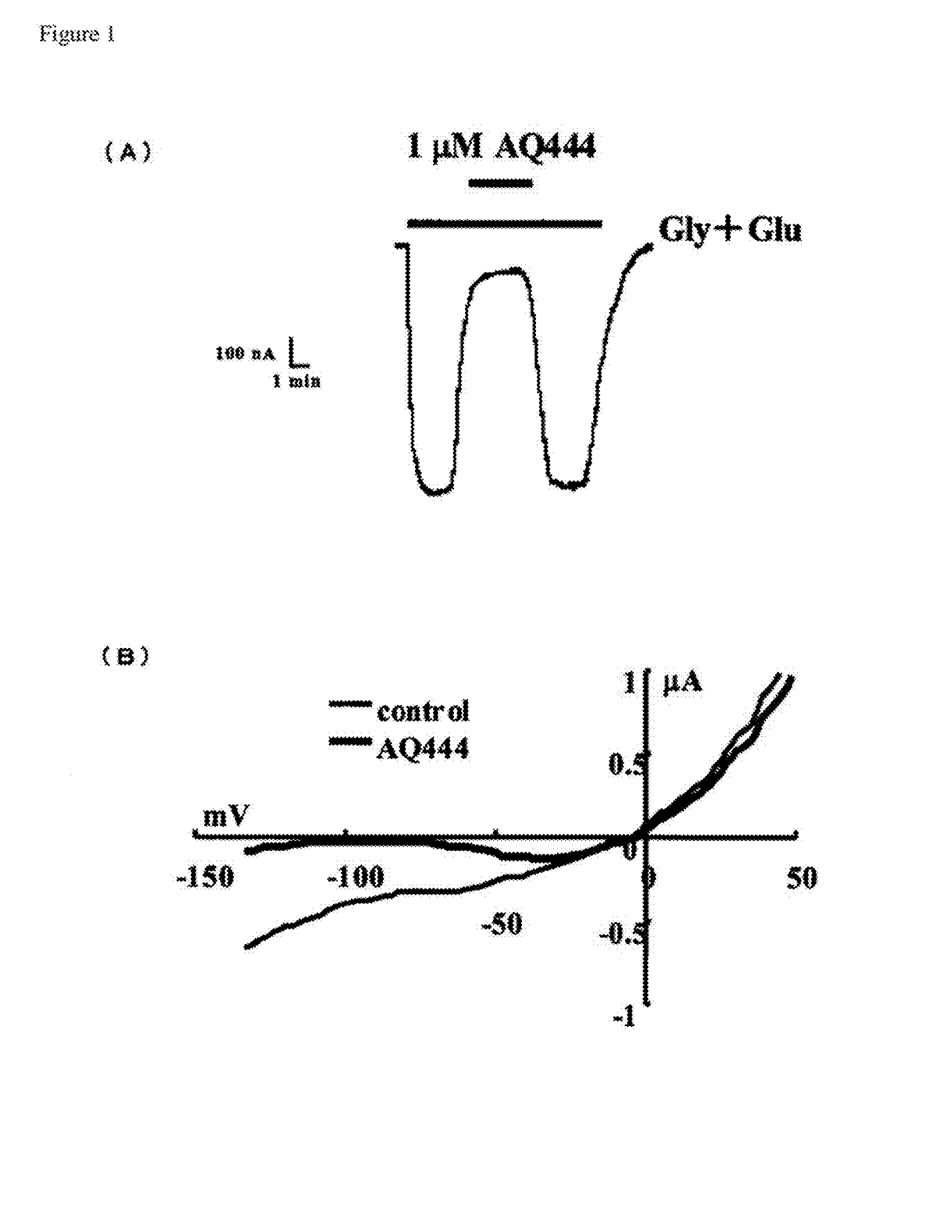

Investigation of Channel Blocking Activity of AQ444 on NMDA Receptors Expressed on *Xenopus oocytes*, and of its Voltage Dependence The cDNA clones for NMDA receptors were used to prepare the cRNAs, which were then injected in *Xenopus oocytes*. The cRNAs of subtype 1 (NR1) and subtype 2 (NR2A) of NMDA receptors were injected in a *Xenopus oocyte* in a ratio of 1:5 (0.1 ng of NR1 and 0.5 ng of NR2A) and incubated in an incubator for several days to express the NMDA receptors on the membrane of the developed egg. The expression was confirmed by a two electrode voltage clamp system. A glass capillary was filled with a 3M potassium chloride solution for use as an electrode, which was then inserted into an egg placed in a perfusion solution to measure a change in membrane potential. The perfusion solution used comprised 100 mM sodium chloride, 2 mM potassium chloride, 1.8 mM barium chloride and 10 mM HEPES, pH 7.5. The electric current through the NMDA receptor in the presence of 10 μM glycine and 10 μM glutamic acid was used as a standard (control) to investigate the channel blocking activity of AQ444. Results are shown in FIG. 1. FIG. 1 (A) shows the results determined under membrane potential clamp at −70 mV. In the figure, the bars denote the timing periods during which glycine and glutamic acid (Gly+Glu) were present with or without the AQ444 added, respectively. In FIG. 1 (A), time and electric current value are denoted along the horizontal and vertical axes, respectively.

As a result as shown in FIG. 1 (A), AQ444 showed channel blocking activity on the NR1/NR2A with the 50% inhibition concentration (IC$_{50}$) of 0.47 μM. This value revealed that AQ444 has about two times stronger channel blocking activity than memantine (IC$_{50}$=0.95 μM) that is commercially available as a cerebral function improving agent.

As shown in FIG. 1 (B), it was found that the channel blocking activity of AQ444 showed voltage dependence according to continuous change in membrane potential of the egg from −150 mV to +10 mV. Since the membrane potential of a cell is normally about −70 mV, it was revealed that AQ444 worked on the cells with static membrane potential and showed channel blocking activity on NMDA receptor.

Example 2

Investigation of Reactivity of AQ444 with Each the NMDA Receptor Subtypes

Figure 2:
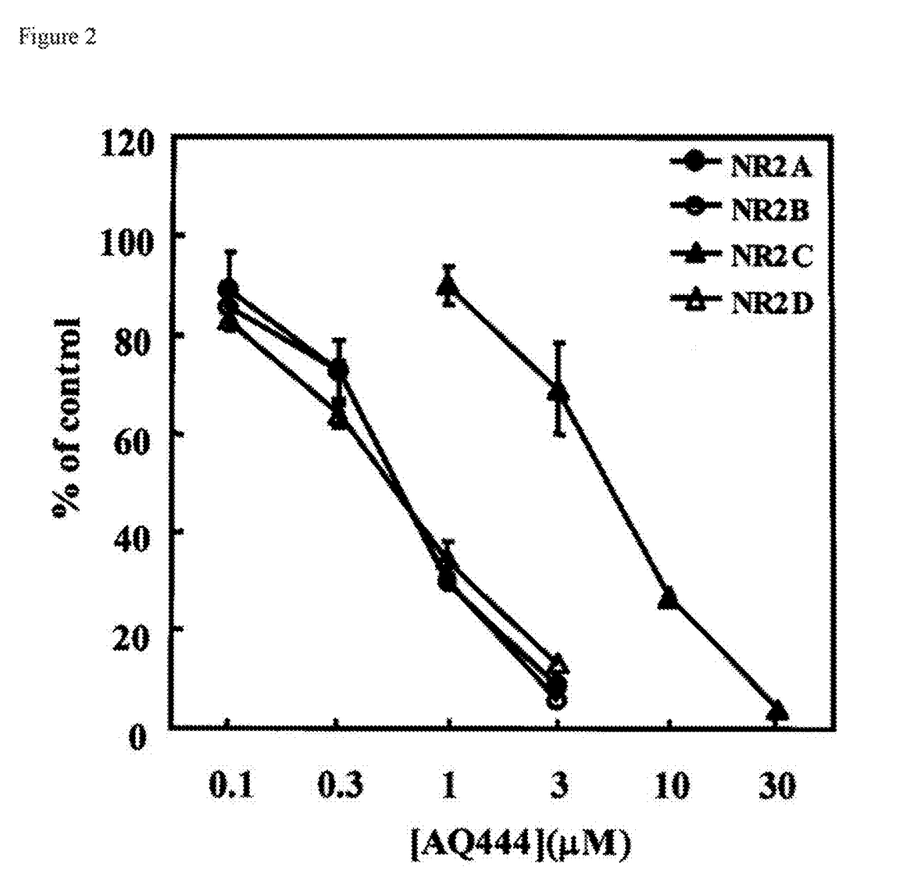
FIG. 2 is a graph showing channel blocking activity of AQ444 on each the NMDA receptor subtypes.

In the same method as shown in Example 1, eggs were injected with the cRNAs for NR1/NR2A (0.1 ng of NR1 and 0.5 ng of NR2A), those for NR1/NR2B (0.1 ng of NR1 and 0.5 ng of NR2B), those for NR1/NR2C (4 ng of NR1 and 20 ng of NR2C), or those for NR1/NR2D (4 ng of NR1 and 20 ng of NR2D) to investigate the reactivity of AQ444 with each the receptors prepared. AQ444 was added to the perfusion solution to get a final concentration of 0.1 to 30 μM. Results obtained are shown in FIG. 2. AQ444 showed channel blocking activity more selectively against NR1/NR2A, NR1/NR2B and NR1/NR2D. Further, the intensities in channel blocking activity against the receptors were in the order of NR1/NR2A=NR1/NR2B=NR1/NR2D>>NR1/NR2C.

Example 3

Figure 3:
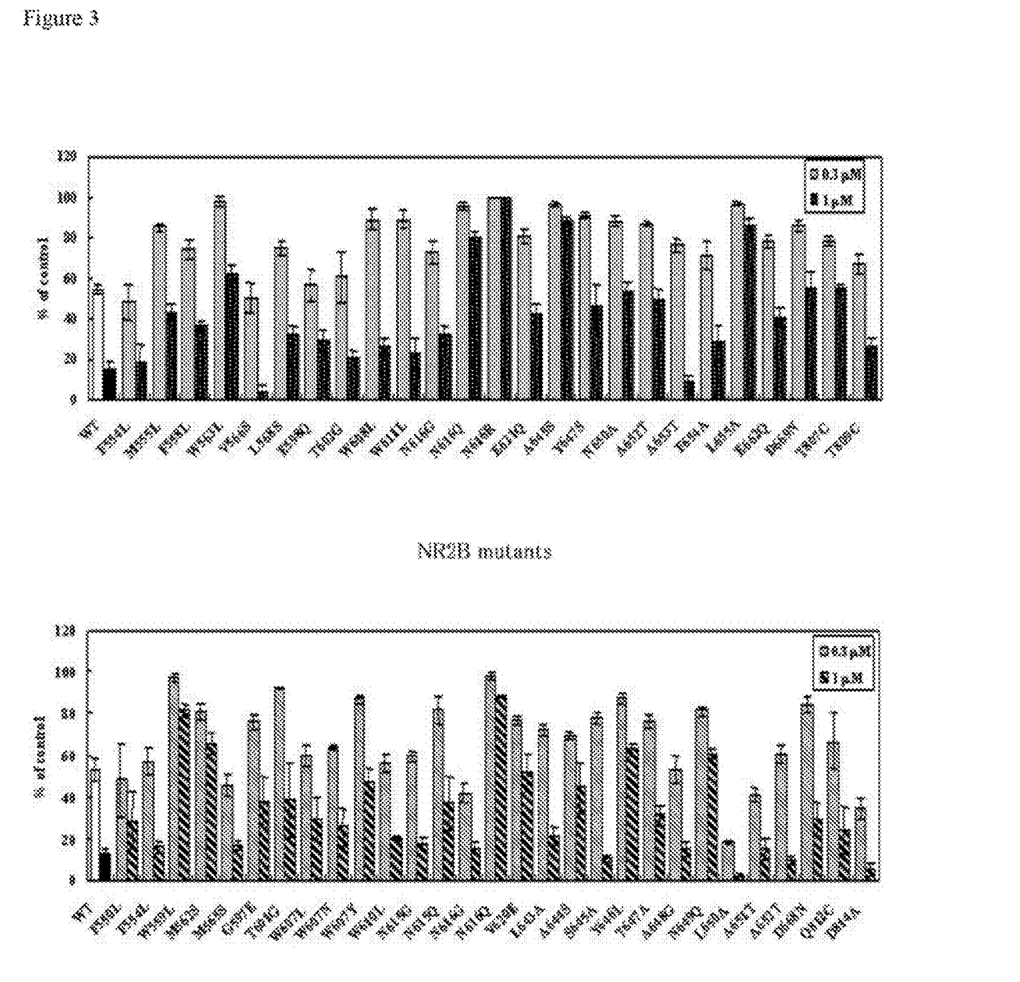
FIG. 3 is a graph showing channel blocking activity of AQ444 on various NMDA receptor mutants.
Figure 4:
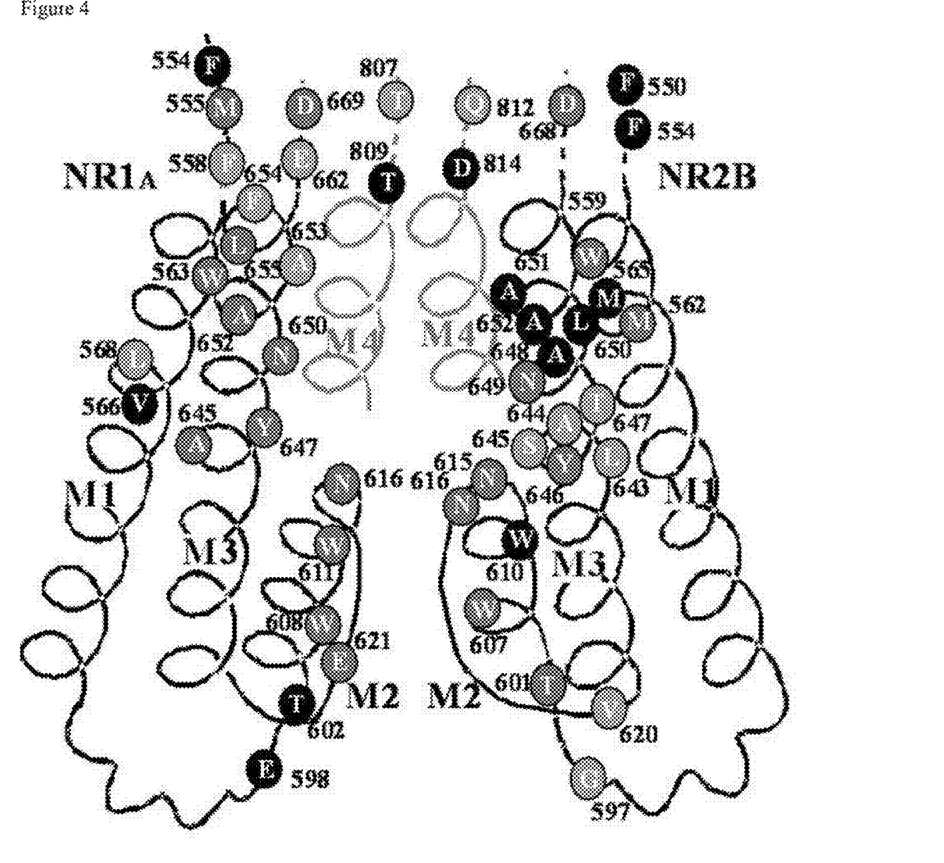
FIG. 4 shows the predicted structural models of NMDA receptors around their channel pores with indicating the amino acid residues involved in channel blocking activity of AQ444.

Investigation of AQ444 Channel Blocking Activity on NMDA Receptor Mutants with Amino Acids Substitutions Site-directed mutagenesis was utilized to construct NMDA receptor mutants with amino acid substitutions. The NMDA receptor mutants were expressed in eggs in the same method as shown in Example 1 to investigate for channel blocking activity of AQ444. Results obtained are shown in FIG. 3. As shown in FIG. 3, both an NR1 mutant with substitution of asparagine for glutamine at position 616 (hereinafter, abbreviated to N616Q) and an NR1 mutant N616R showed significantly decreased channel blocking activity. NR2B mutants, that are N615Q and N616Q, also showed significantly decreased channel blocking activity. These residues are located at the site in the M2 region of the NMDA receptor which is considered to define the size of a channel pore, suggesting that they are strongly associated with the channel blocking activity of AQ444. Other relevant amino acid residues on the NMDA receptors are shown in FIG. 4 together with their models.

Example 4

Channel Blocking Activity of Carbazole Spermine on NMDA Receptors Expressed on *Xenopus oocytes*

In the same method as shown in Example 1, carbazole spermine was used in replace of AQ444 to determine its channel blocking activity. As a result, the IC$_{50}$ of carbazole spermine was 15 μM. This value revealed that carbazole spermine has about six times stronger channel blocking activity than memantine ($IC_{50}$=0.95 μM) which is commercially available as a cerebral function improving agent.

DBA444 and DDBA444 containing an azepine ring and a 4,5-dihydroazepine ring respectively inhibited the NMDA receptor activity in a voltage-dependent manner. The both compounds had their respective $IC_{50}$s of 0.24 and 0.072 μM at −70 mV. Consequently, it was found that the both compounds showed about 4 times and 13 times stronger channel blocking activity respectively than memantine. Further, DBA444 and DDBA444 had their respective $IC_{50}$s of 132 μM and 133 μM in cytotoxicity, which were comparable to memantine with $IC_{50}$ of 147 μM. Therefore, DBA444 and DDBA444 were expected to effect with a smaller amounts and less side effect than memantine.

As demonstrated above, it was revealed that the present invention can provide a novel compound having NMDA receptor channel blocking activity and a pharmaceutical agent comprising the compound.

INDUSTRIAL APPLICABILITY

Along with the aging society, the population of people suffering from diseases which bring impairment in higher cerebral functions, such as cerebrovascular disorders and Alzheimer's disease, has been increasing year by year. A compound provided by the present invention and a pharmaceutical agent using the same have industrial applicability to be used for an agent of preserving brain functions. There is no doubt that the novel agent of preserving brain functions thus developed would bring improved QOL (Quality of Life) to the patients, and moreover, to the caretakers, and thus would make an immensurable contribution in medical treatment for the elderly.

BRIEF DESCRIPTION OF THE DRAWINGS

FIG. 1 (A) shows a waveform indicating that addition of AQ444 resulted in suppression of current flow through the NMDA receptors expressed on *Xenopus oocytes*.

FIG. 1 (B) is a graph showing voltage-dependent channel blocking activity of AQ444.

What is claimed is:

1. A pharmaceutical formulation comprising a) a compound represented by the following formula (1), a salt thereof, or a hydrate of the compound or the salt,

[chemical formula 1]

(1)

wherein the B-ring, condensed to the A-ring and the C-ring, is azepine, $R_1$-$R_5$ are each independently formyl, acyl, hydrogen, alkyl, alkoxy, halogen, hydroxy, amino, aryl or carboxamido, and at least either of $R_1$ or $R_2$ is one carboxamide group having a polyamine structure containing three or more amino groups, wherein an amino group of any carboxamido group is excluded, and $R_1$-$R_5$ are identical or different, and b) a pharmaceutically acceptable carrier.

2. A pharmaceutical formulation comprising a) a compound is represented by formula (4), a salt thereof, or a hydrate of the compound or the salt,

[chemical formula 4]

(4)

and b) a pharmaceutically acceptable carrier.

3. A compound represented by the following formula (1), or a pharmaceutically acceptable salt thereof,

[chemical formula 6]

(1)

wherein the B-ring, condensed to the A-ring and the C-ring, is azepine, $R_1$-$R_5$ are each independently formyl, acyl, hydrogen, alkyl, alkoxy, halogen, hydroxy, amino, aryl or carboxamido, and at least either of $R_1$ or $R_2$ is one carboxamide group having a polyamine structure containing three or more amino groups, wherein an amino group of any carboxamido group is excluded, and $R_1$-$R_5$ are identical or different.

4. A compound represented by formula (4),

[chemical formula 9]

(4)

5. A compound represented by the following formula (1), a salt thereof, or a hydrate of the compound or the salt,

[chemical formula 1]

(1)

wherein the B-ring, condensed to the A-ring and the C-ring, is azepine, $R_1$-$R_5$ are each independently formyl, acyl, hydrogen, alkyl, alkoxy, halogen, hydroxy, amino, aryl or carboxamido, and at least either of $R_1$ or $R_2$ consists of a single carboxamide group and a polyamine structure containing three or more amino groups, wherein an amino group of any carboxamido group is excluded, and $R_1$-$R_5$ are identical or different and wherein said polyamine structure is directly bonded to said single carboxamide group.

6. The pharmaceutical formulation of claim 1, wherein the polyamine structure is a non-aromatic polyamine structure.

7. The compound of claim 5, wherein the polyamine structure is a non-aromatic polyamine structure.

* * * * *